(12) United States Patent
Camps et al.

(10) Patent No.: US 8,744,584 B2
(45) Date of Patent: Jun. 3, 2014

(54) ELECTRICAL STIMULATION OF THE COLON TO TREAT CHRONIC CONSTIPATION

(71) Applicant: Medtronic, Inc., Minneapolis, MN (US)

(72) Inventors: Antoine Camps, Gulpen-Wittem (NL); Nathalie Virag, Monnaz (CH); Mattia Bertschi, La Conversion (CH); Pavel Kucera, Lausanne (CH)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/925,935

(22) Filed: Jun. 25, 2013

(65) Prior Publication Data

US 2013/0345781 A1   Dec. 26, 2013

Related U.S. Application Data

(60) Division of application No. 11/620,529, filed on Jan. 5, 2007, now abandoned, which is a continuation of application No. 10/422,077, filed on Apr. 23, 2003, now abandoned.

(51) Int. Cl.
*A61N 1/36* (2006.01)
(52) U.S. Cl.
USPC ............................................................ 607/40

(58) Field of Classification Search
USPC ................................................ 607/40, 41, 133
See application file for complete search history.

(56) References Cited

U.S. PATENT DOCUMENTS

| | | | |
|---|---|---|---|
| 5,292,344 A * | 3/1994 | Douglas | 607/40 |
| 5,417,719 A | 5/1995 | Hull | |
| 5,690,691 A * | 11/1997 | Chen et al. | 607/40 |
| 6,236,892 B1 | 5/2001 | Feler | |
| 6,238,423 B1 * | 5/2001 | Bardy | 607/40 |
| 6,243,607 B1 | 6/2001 | Mintchev | |
| 6,324,435 B1 | 11/2001 | Shchervinsky | |
| 6,449,511 B1 * | 9/2002 | Mintchev et al. | 607/40 |
| 6,826,428 B1 * | 11/2004 | Chen et al. | 607/40 |
| 6,965,798 B2 | 11/2005 | Kim | |
| 7,221,981 B2 | 5/2007 | Gliner | |

* cited by examiner

*Primary Examiner* — George Evanisko
(74) *Attorney, Agent, or Firm* — Mueting, Raasch & Gebhardt, P.A.

(57) ABSTRACT

The invention is directed to techniques for stimulating a colon of a patient to relieve chronic constipation. Specifically, a colon stimulation system applies one or more electrical stimuli to the colon of the patient in order to induce peristaltic activity in the colon to relieve chronic constipation. In accordance with the invention, the colon stimulation system induces peristaltic activity in the colon by applying an electrical stimulus to the colon to cause a portion of the colon to contract to a contracted state and removing the electrical stimulus to cause the colon to relax. While in the contracted state, the colon is substantially fully contracted.

20 Claims, 7 Drawing Sheets

ELECTRICAL STIMULATION OF THE COLON TO TREAT CHRONIC CONSTIPATION

This is a divisional application of U.S. patent application Ser. No. 11/620,529, filed Jan. 5, 2007, which is a continuation of U.S. patent application Ser. No. 10/422,077, filed Apr. 23, 2003, the entire contents of which are incorporated herein by reference.

FIELD OF THE INVENTION

The invention relates to medical devices, and more particularly, to devices that stimulate a colon of a patient to treat constipation.

BACKGROUND OF THE INVENTION

Chronic constipation refers to a decreased number of bowel movements and/or difficulties evacuating the rectum, including excessive straining or hard stools. Constipation is a major problem for many individuals and frequently causes extreme discomfort to the afflicted, including discomfort during passage of stools, a constant feeling of the need to pass stool, and the like.

Chronic constipation may result from changes in diet, decrease in physical activity, dehydration, diseases of the bowel, neurological diseases, congenital diseases, medications, and physical injury. Conventional therapies for chronic constipation include consumption of laxatives, special diets, colon ablation surgery, and the like.

BRIEF SUMMARY OF THE INVENTION

In general, the invention is directed to techniques for stimulating a colon of a patient to relieve chronic constipation. Specifically, a colon stimulation system applies electrical stimuli to the colon of the patient in order to induce peristaltic activity in the colon to relieve chronic constipation. In accordance with the invention, the colon stimulation system induces peristaltic activity in the colon by applying an electrical stimulus to the colon to cause a portion of the colon to contract to a contracted state and removing the electrical stimulus to cause the colon to relax. As will be described, while in the contracted state, the colon is substantially fully contracted.

The colon stimulation system includes a stimulus generator to generate electrical stimuli for application to the colon via one or more electrodes placed in contact with the colon. More specifically, one or more leads couple the stimulus generator to the electrodes in contact with the colon. The electrodes are in contact with an outer portion of a cecum of the colon. However, in alternate embodiments, the electrodes may be deployed elsewhere along the colon such as along the ascending colon, the transverse colon, the descending colon or the sigmoid colon. The electrodes may be anchored to the colon using a needle to advance the electrodes into the muscular tissue of the colon, via one or more sutures or via an adhesive patch.

The colon stimulation system applies electrical stimuli to the colon of the patient via the electrodes and leads in order to induce peristaltic activity in the colon to relieve chronic constipation. The peristaltic activity in the colon moves stool through the colon towards the rectum for exit out of the patient via the anal canal. More specifically, the electrical stimuli applied to the colon via the electrodes and leads cause a portion of colon proximate the electrodes of the leads to substantially fully contract, i.e., contract to the contracted state. For example, the stimulus generator may apply the electrical stimuli to the colon for a prolonged period of time, e.g., sixty seconds, in order to cause the colon to substantially fully contract. When the stimulus generator removes or discontinues the electrical stimulus, the contracted portion of the colon relaxes to a non-contracted state. During the contraction and relaxation of the colon a natural colonic activity is triggered thereby induce peristaltic activity.

The colon stimulation system can be configured to apply one or more electrical stimuli to the colon in accordance with numerous stimulation algorithms. In one embodiment, the colon stimulation system applies multiple electrical stimuli to the colon substantially simultaneously. For example, the colon stimulation system applies electrical stimuli to the colon via a plurality of electrodes and leads at substantially the same time. In this manner, the stimulation algorithm separates the electrical stimuli applied to the colon in space, e.g., at different locations along the colon. The application of the electrical stimuli to the colon substantially simultaneously causes the portion of the colon proximate the electrodes of the leads to contract to a substantially fully contracted state at substantially the same time. Alternatively, the colon stimulation system may selectively apply stimulation to the colon via a particular subset of the electrodes and leads. For example, the colon stimulation system may apply an electrical stimulus to the colon via electrodes of a single lead.

Further, the colon stimulation system may apply a series of electrical stimuli to the colon. For example, the colon stimulation system may apply a first set of electrical stimuli substantially simultaneously to the colon via the electrodes and leads to cause a portion the colon to contract to a contracted state, remove the electrical stimuli to cause the colon to relax, and then apply a second set of electrical stimuli substantially simultaneously to the colon via the electrodes and leads to cause the portion of the colon to contract to the contracted state again. In this manner, the stimulation algorithm causes the electrical stimuli to be applied to the colon at different locations along the colon, and further causes the electrical stimuli to be applied at different times as well. Although in the example described the colon stimulation system only applies two sets of electrical stimuli to the colon separated by a period of non-stimulation, the colon stimulation system can apply any number of sets of electrical stimuli to the colon with each set of electrical stimuli followed by a non-stimulation period. The stimulus generator may remove the electrical stimulus from the colon for a long enough period of time to allow the colon to relax to a substantially non-contracted state. However, in some cases, the stimulus generator applies the second set of electrical stimuli to the colon before the colon relaxes to a fully non-contracted state, i.e., while the colon is still partially contracted.

In another embodiment, the colon stimulation system can be configured to apply electrical stimuli to the colon sequentially along the colon. For example, the colon stimulation system applies an electrical stimulus to the colon via electrodes of a first lead, followed by subsequent application of an electrical stimulus via electrodes of a second lead, and a further subsequent application of an electrical stimulus via electrodes of a third lead. The sequential application of the electrical stimuli to the colon via electrodes of the three leads causes portions of the colon proximate respective the electrodes of the leads to enter the contracted state. Particularly, the portion of the colon proximate electrodes of the first lead begins to contract, followed by the portion of the colon proximate electrodes of the second lead and then the portion of the colon proximate electrodes of the third lead. In this manner, the contraction of the colon "moves" along the colon toward the rectum.

In the same way, the relaxation of the colon "moves" along the colon toward the rectum. Specifically, the colon stimulation system removes the electrical stimulus to the portion of the colon proximate the electrodes of the first lead to allow of the portion of the colon proximate electrodes the first lead to relax. Likewise, the colon stimulation system sequentially removes the electrical stimuli to the portions of the colon proximate the electrodes of the second and third leads, allowing the portion of the colon proximate the electrodes of the second lead and the portion of the colon proximate the electrodes of the third lead to sequentially relax. Further, the colon stimulation system may apply sets of electrical stimuli to the colon via the plurality of electrodes and leads. For example, the colon stimulation system may apply to the colon a first set of sequential electrical stimuli, which last for approximately 1 minute, via the plurality of leads followed by a period of relaxation, e.g., 2-3 minutes, and then apply a second set of sequential electrical stimuli to the colon via the leads.

In one embodiment, the invention provides a system comprising a stimulus generator to generate an electrical stimulus and at least one electrode in contact with a colon of a patient to apply the electrical stimulus to the colon. The system is configured to cause the colon to undergo peristaltic activity by applying the electrical stimulus to the colon to cause a portion of the colon to contract to a contracted state where a portion of the colon is substantially fully contracted, and by removing the electrical stimulus to cause the colon to relax.

In another embodiment, the invention provides a method comprising applying an electrical stimulus to the colon to cause a portion of the colon to contract to a contracted state, the portion of the colon being substantially fully contracted in the contracted state, and removing the electrical stimulus to cause the colon to relax.

In a further embodiment, the invention provides a computer-readable medium comprising instructions that cause a processor to apply an electrical stimulus to the colon to cause a portion of the colon to contract to a contracted state, the portion of the colon being substantially fully contracted in the contracted state and remove the electrical stimulus to cause the colon to relax.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
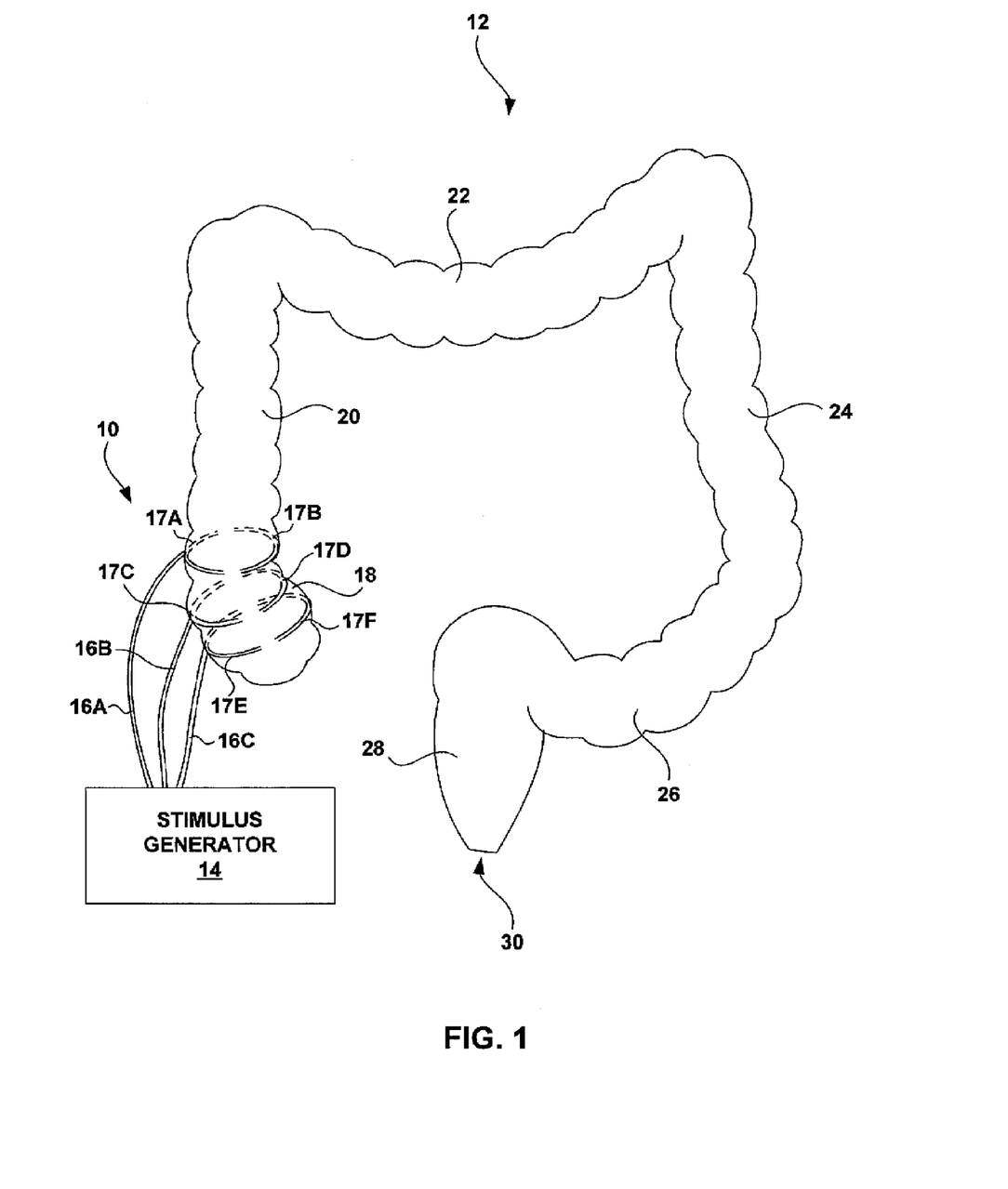
FIG. 1 is a schematic diagram illustrating a colon stimulation system in conjunction with a colon of a patient.

FIG. 1 is a schematic diagram illustrating a colon stimulation system 10 in conjunction with a colon 12 of a patient. Colon stimulation system 10 applies electrical stimuli to colon 12 of the patient in order to induce peristaltic activity in colon 12 to relieve chronic constipation. Specifically, in accordance with the invention, colon stimulation system 10 induces peristaltic activity in colon 12 by applying an electrical stimulus to colon 12 to cause a portion of colon 12 to contract to a contracted state and removing the electrical stimulus to cause colon 12 to relax. As will be described, while in the contracted state, colon 12 is substantially fully contracted.

Colon stimulation system 10 includes a stimulus generator 14 to generate electrical stimuli for applying to colon 12 via leads 16A-16C ("leads 16"). As shown in the example illustrated in FIG. 1, leads 16 couple stimulus generator 14 to electrodes 17A-17F ("electrodes 17") in contact with colon 12. More specifically, leads 16 couple stimulus generator 14 to respective electrode pairs in contact with colon 12. For example, lead 16A couples electrodes 17A and 17B in contact with colon 12 to stimulus generator 14. Electrodes 17A and 17B are placed in contact with colon 12 and may be arranged such that electrode 17A is diametrically opposite of electrode 17B.

The arrangement of leads 16 and electrodes 17 shown in FIG. 1 is for purposes of illustration, and the invention is not limited to the colon stimulation system 10 shown in FIG. 1. In some embodiments of colon stimulation system 10, for example, a single lead may include a plurality of conductors that couple a plurality of electrodes to stimulus generator 14. In other embodiments, each electrode may be coupled to stimulus generator 14 by a dedicated lead. In the latter case, a pair of leads may be deployed for each section of colon 12 to which an electrical stimulus is applied. In other words, a pair of electrodes is deployed on diametrically opposite sides of colon 12, with each electrode coupled to stimulus generator 14 by a dedicated lead.

As will be described, leads 16 may include a needle that advances electrodes 17 of the respective lead 16 into the muscular tissue of colon 12. For example, a physician can place and fixate electrodes 17 in the muscular tissue of the colon by meandering leads 16 through the tissue via the needle. Alternatively, electrodes 17 may be fixated on colon 12 via one or more sutures placed around electrodes 17. In further embodiments, electrodes 17 may be fixated to colon 12 via an adhesive patch that includes electrodes 17 embedded within or otherwise coupled to the adhesive patch.

In the example illustrated in FIG. 1, electrodes 17 are in contact with an outer portion of colon 12 and, more particularly, an outer portion of a cecum 18 of colon 12. However, in other embodiments, electrodes 17 can be in contact with an inner portion of colon 12. Further, electrodes 17 can be deployed elsewhere along colon 12. For example, electrodes can be deployed along ascending colon 20, transverse colon 22, descending colon 24 or sigmoid colon 26.

Stimulus generator 14 generates the electrical stimuli for apply to colon 12 via leads 16 and electrodes 17. More specifically, stimulus generator 14 generates electrical pulses that are applied via electrodes 17 to colon 12. An exemplary type of electrical stimuli generated by stimulus generator 14 includes monophasic square waves. However, stimulus generator 14 can generate other types of electrical stimuli, such as triangle waves, sine waves, or exponential decay waves. Further, the electrical stimuli generated by stimulus generator 14 may be biphasic or triphasic. In some embodiments, stimulus generator 14 is an implantable stimulus generator, such as a neurostimulator.

As described, colon stimulation system 10 applies electrical stimuli to colon 12 of the patient in order to induce peristaltic activity in colon 12 to relieve chronic constipation. The peristaltic activity in colon 12 moves stool through colon 12 towards rectum 28 for exit out of the patient via anal canal 30. In accordance with the invention, colon stimulation system 10 induces peristaltic activity in colon 12 by applying an electrical stimulus to colon 12 to cause a portion of colon 12 to contract to a contracted state and removing the electrical stimulus to cause the portion of colon 12 to relax. More specifically, the electrical stimuli applied to colon 12 via electrodes 17 cause a portion of colon 12 proximate electrodes 17 to substantially fully contract, i.e., contract to the contracted state. For example, stimulus generator 14 may apply the electrical stimuli to colon 12 for a prolonged period of time, e.g., sixty seconds, in order to cause colon 12 to substantially fully contract. During the contraction and relaxation of colon 12 a natural colonic activity is triggered thereby induce peristaltic activity.

Colon stimulation system 10 can be configured to apply one or more electrical stimuli to colon 12 in accordance with numerous stimulation algorithms. In one embodiment, colon stimulation system 10 applies multiple electrical stimuli to colon 12 substantially simultaneously. For example, stimulus generator 14 applies electrical stimuli to colon 12 via leads 16A, 16B, and 16C at substantially the same time. In this manner, the stimulation algorithm separates the electrical stimuli applied to colon 12 in space, e.g., at different locations along colon 12. The application of the electrical stimuli substantially simultaneously causes the portion of colon 12 proximate to each of electrodes 17 to contract to a substantially fully contracted state at substantially the same time. Although colon stimulation system 10 is described as applying electrical stimuli via all of leads 16, colon stimulation system 10 may selectively apply stimulation to colon 12 via a particular subset of leads 16. For example, colon stimulation system 10 may apply an electrical stimulus to colon 12 via only electrodes 17A and 17B of lead 16A.

Further, colon stimulation system 10 may apply a series of electrical stimuli to the electrodes 17. For example, the colon stimulation system 10 may apply a first set of electrical stimuli substantially simultaneously to colon 12 via leads 16 to cause a portion colon 12 to contract to a contracted state, remove the electrical stimuli to cause colon 12 to relax, and then apply a second set of electrical stimuli substantially simultaneously to colon 12 via leads 16 to cause the portion of colon 12 to contract to the contracted state again. In this manner, the stimulation algorithm causes the electrical stimuli to be applied to colon 12 at different locations along colon 12, and further causes the electrical stimuli to be applied at different times as well. Although in the example described colon stimulation system 10 only applies two sets of electrical stimuli to colon 12 separated by a period of non-stimulation, colon stimulation system 10 can apply any number of sets of electrical stimuli to colon 12 with each set of electrical stimuli followed by a non-stimulation period. Further, colon stimulation system 10 may remove or discontinue the electrical stimulus from colon 12 for a long enough period of time to allow colon 12 to relax to a substantially non-contracted state. However, in some cases, colon stimulation system 10 applies the second set of electrical stimuli to colon 12 before colon 12 relaxes to a fully non-contracted state, i.e., while colon 12 is still partially contracted.

In another embodiment, colon stimulation system 10 can be configured to apply electrical stimuli to colon 12 sequentially along colon 12. For example, stimulus generator 14 applies an electrical stimulus to colon 12 via electrodes 17E and 17F of lead 16C, followed by subsequent application of an electrical stimulus via electrodes 17C and 17D of lead 16B, and a further subsequent application of an electrical stimulus via electrodes 17A and 17B of lead 16A. The sequential application of the electrical stimuli to colon 12 via leads 16 causes portions of colon 12 proximate respective leads 16 to enter the contracted state. Particularly, the portion of colon 12 proximate electrodes 17E and 17F begins to contract followed by the portion of colon 12 proximate electrodes 17C and 17D and then the portion of colon 12 proximate electrodes 17A and 17B. In this manner, the contraction of colon 12 "moves" along colon 12 toward rectum 28.

In the same way, the relaxation of colon 12 "moves" along colon 12 toward rectum 28. Specifically, colon stimulation system 10 removes the electrical stimulus to the portion of colon 12 proximate electrodes 17E and 17F to allow of the portion of colon 12 proximate electrodes 17E and 17F to relax. Likewise, colon stimulation system 10 sequentially removes the electrical stimuli to the portions of colon 12 proximate electrodes 17C and 17D as well as 17A and 17B, allowing the portion of colon 12 proximate electrodes 17C and 17D and the portion of colon 12 proximate electrodes 17A and 17B to sequentially relax. Further, colon stimulation system 10 may apply sets of electrical stimuli to colon 12 via leads 16 and electrodes 17. For example, colon stimulation system 10 may apply a first set of sequential electrical stimuli to colon 12 via leads 16 followed by a period of relaxation, e.g., 2-3 minutes, and then apply a second set of sequential electrical stimuli to colon 12 via leads 16.

Although colon stimulation system 10 FIG. 1 is described as having three leads 16 to place respective electrodes 17 in contact with colon 12, colon stimulation system 10 may include any number of leads or any number of electrodes in contact with colon 12. In some embodiments, for example, colon stimulation system 10 may include only a single lead with a single pair of electrodes in contact with colon 12. Although colon stimulation system 10 is described in terms of applying one or more electrical stimuli directly to the muscular tissue of colon 12, the techniques of the invention may be used in applying the electrical stimuli to nerves that control contraction of colon 12.

Figure 2:
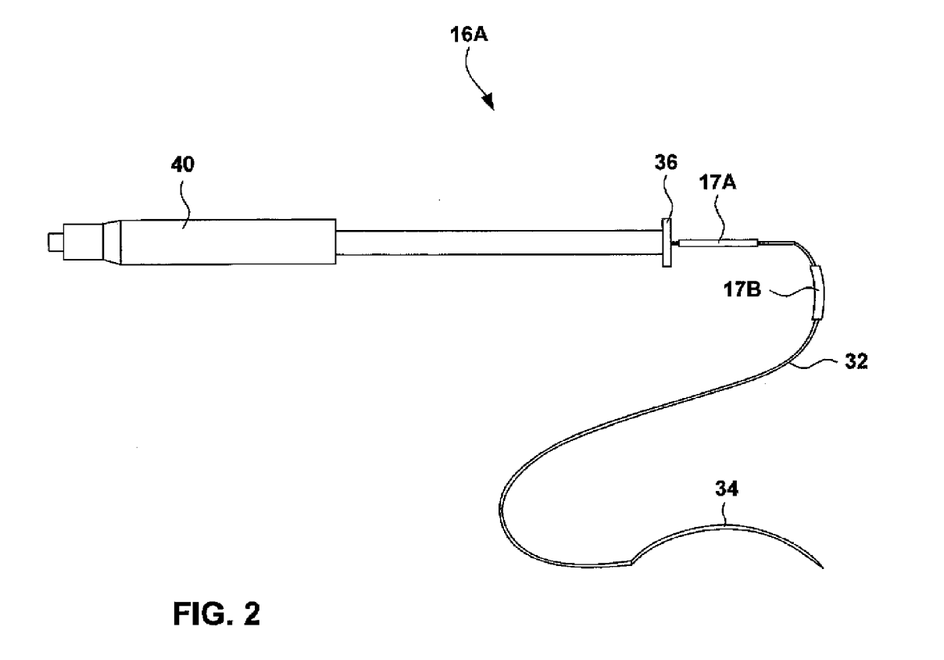
FIG. 2 is a schematic diagram illustrating an exemplary lead that fixates one or more electrodes in contact with a colon of a patient.

FIG. 2 is a schematic diagram illustrating an exemplary lead, such as lead 16A of FIG. 1. Lead 16A includes a lead body 32 and electrodes 17A and 17B ("electrodes 17"). As described above, lead body 32 couples stimulus generator 14 (not shown in FIG. 2) to electrodes 17 in contact with colon 12. More specifically, electrodes 17 are sized and spaced on lead body 32 to be deployed diametrically opposite one another on colon 12. Electrodes 17 may be rigid or flexible.

Further, when deployed, electrodes 17A and 17B extend around a portion of colon 12. Although electrodes 17 are not long enough to not encircle the circumference of the portion of colon 12, electrodes 17 are sized to contact a substantial share of the circumference, enabling electrodes 17 to stimulate colon 12 to produce a stronger, fuller contraction. A length of each of electrodes 17 can be slightly less than half of the circumference of the portion of colon 12 to which electrodes 17 contact. Electrodes 17, however, do not constrict movements of colon 12.

Lead 16A fixates electrodes 17 to muscular tissue of colon 12. More specifically, lead 16A may include a needle 34 used to advance electrodes 17 into the muscular tissue of colon 12. For example, a physician can place and anchor electrodes 17 in the muscular tissue of the colon by meandering lead body 32 through the muscular tissue via needle 34. Alternatively, needle 34 may advance electrodes 17 straight through the tissue and the shape of electrodes 34 may help anchor the electrodes to colon 12. Electrodes 17 may be take numerous shapes including a straight shape, a meandering shape, a curved shape and the like, and the shape of the electrode may help keep the electrode in place. Alternatively, electrodes 17 may be anchored to colon 12 via one or more sutures placed around electrodes 17.

Lead body 32 may also include anchoring mechanisms, such as fixation mechanism 36. Fixation mechanism 36 may include, for example, tines or other obtrusions that lodge in the tissue of colon 12 to anchor lead body 32 and electrodes 17. Lead body 32 may also include fixation mechanisms elsewhere along lead body 32, such as near electrode 17B or between electrodes 17A and 17B.

Lead 16A further includes a connector 40 that couples lead 16A to stimulus generator 14. Stimulus generator 14 applies electrical stimuli to colon 12 via lead 16A and, more particularly, via electrodes 17A and 17B. The electrical stimuli to colon 12 of the patient induce peristaltic activity in colon 12 to relieve chronic constipation in accordance with the invention.

Lead body 32 may further include a coating that elutes a therapeutic agent. The coating may include a steroid coating to enhance the stimulation properties of colon 12, a anti-bacterial coating to reduce the risk of infection of the tissue of colon 12 where electrodes 17 are fixated and the like.

The example illustrated in FIG. 2 is for exemplary purposes. In other embodiments, lead 16A may include conductors to support any number of electrodes 17. For example, instead of lead 16A having a pair of electrodes, lead 16A may include only a single conductor, making lead 16A capable of coupling only one electrode to stimulus generator 14. Each individual electrode may be separately deployed in the muscular tissue of colon 12.

Figure 3:
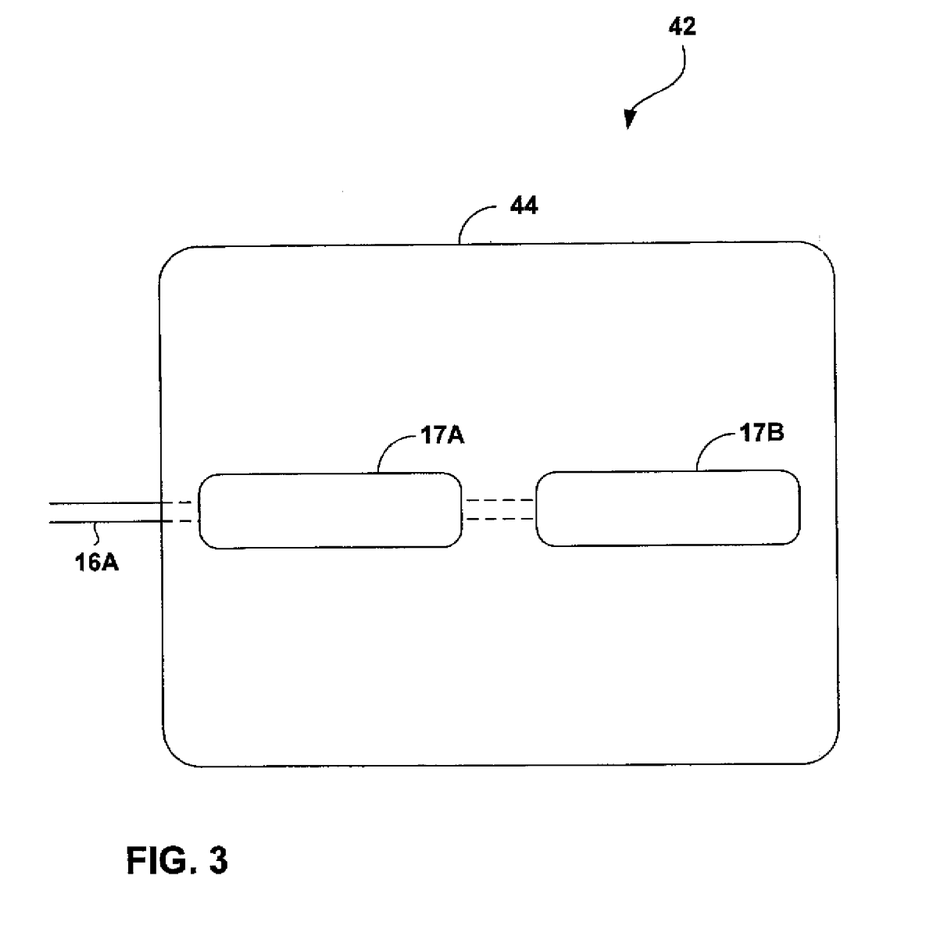
FIG. 3 is a schematic diagram illustrating an exemplary patch lead to place of electrodes on the colon.

FIG. 3 is a schematic diagram illustrating a patch lead 42 for placement of electrodes 17A and 17B ("electrodes 17") on colon 12. Patch lead 42 includes a patch body 44 that is formed from a biocompatible material, such as silicone, and includes electrodes 17 embedded within patch body 44. Lead 16A may include separate conductors for electrodes 17A and 17B and may also be embedded in patch body 44. Patch body 44 is sized to wrap around a portion of colon 12, and electrodes 17 are sized and spaced relative to one another on patch lead 42 such that when patch lead 42 is wrapped around a portion of colon 12, electrodes 17 are deployed diametrically opposite one another.

Further, electrodes 17A and 17B are sized to contact a substantial share of the circumference of the portion of colon 12 around which patch lead 42 wraps, enabling electrodes 17 to stimulate colon 12 to produce a stronger, fuller contraction. A length of each of electrodes 17 can be slightly less than half of the circumference of the portion of colon 12 to which electrodes 17 contact. Patch lead 42 and electrodes 17, however, do not constrict movements of colon 12.

Patch lead 42 defines a contact side that comes in contact with colon 12. FIG. 3 shows the contact side of patch lead 42. The surface of the contact side may include a biocompatible adhesive that causes patch lead 42 to adhere to colon 12. For example, patch lead 42 may have a surface that includes one or more biodegradable adhesives. Adhering electrodes 17 atraumatically to colon 12 via patch lead 42 reduces tissue damage to colon 12 caused by attaching electrodes 17 to or within the tissue of colon 12. The surface of the contact side may further include a coating that elutes a therapeutic agent to improve stimulation properties of electrodes 17 over time or reduce the risk of infection near the area patch lead 42 is placed. For example, patch lead 42 includes a steroid to enhance the stimulation properties of electrodes 17. In another example, patch lead 42 includes anti-bacterial medication to reduce the risk of infection of colonic tissue.

Figure 4:
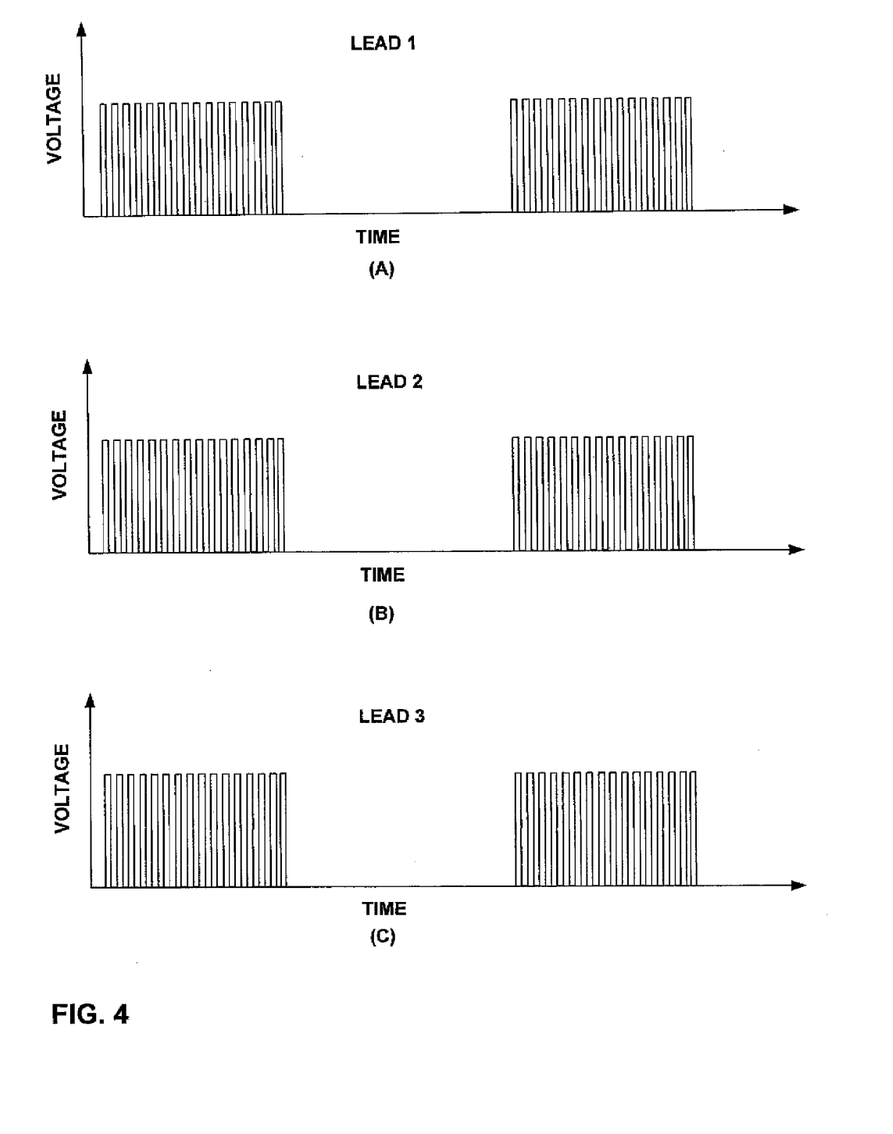
FIG. 4 is a timing diagram illustrating an exemplary stimulation algorithm for applying electrical stimuli to a colon of a patient via a plurality of leads.

FIG. 4 is a timing diagram illustrating an exemplary stimulation algorithm for applying electrical stimuli to a colon 12 of a patient via a plurality of leads. As illustrated in the example of FIG. 4, colon stimulation system 10 applies electrical stimuli substantially simultaneously to colon 12 via leads 1, 2, and 3. Leads 1, 2, and 3 may correspond, for example, to leads 16A-16C illustrated in FIG. 1, respectively.

As shown, colon stimulation system 10 applies, via each of the leads, a first set of electrical stimuli to colon 12. Colon stimulation system 10 removes the stimulation for a period of time, then applies a second set of electrical stimuli to colon 12. Colon stimulation system 10 may, for example, apply the first set of electrical stimuli to colon 12 for approximately 60 seconds, remove the electrical stimuli from colon 12 for approximately 90 seconds, and then apply the second set of electrical stimuli to colon 12 for approximately 60 seconds.

As described above, when colon stimulation system 10 applies the first and second set of electrical stimuli to colon 12, portions of colon 12 proximate to the respective leads contract to a contracted state in which the portions of colon 12 are substantially fully contracted. When colon stimulation system 10 removes the electrical stimuli, the portions of colon 12 proximate the leads relax from the contracted state to a fully or partially non-contracted state. The contraction and relaxation actions of colon 12 induce natural peristaltic activity within colon 12 in order to relieve chronic constipation.

The length of time during which colon stimulation system 10 applies electrical stimuli to colon 12 may vary dramatically. Colon stimulation system 10 may apply the electrical stimuli to colon 12 for anywhere between 10-90 seconds. Further, the length of the interval between applications of stimuli may also vary significantly. For example, colon stimulation system 10 may refrain from providing stimuli for 1-3 minutes (60-180 seconds). In some embodiments, colon 12 may not have an opportunity to relax to a completely non-contracted state during this interval, i.e., colon 12 may be partially contracted upon application of a subsequent set of electrical stimuli.

In the example of FIG. 4, an electrical stimulus applied to colon 12 comprises a set of monophasic square waves, rather than a single sustained stimulus. Stimulation with a set of stimuli produces substantially the same effect on colon 12 as a single sustained stimulus, but places a lesser power demand upon stimulus generator 14 than a single sustained stimulus. In other embodiments, other types of electrical stimuli may be applied to colon 12, including one or more triangle waves, exponential decay waves, sine waves, and the like. Further, the electrical stimuli may be biphasic or triphasic.

The electrical stimuli may further vary in amplitude, frequency and pulse width. A stimulus depicted in FIG. 4, for example, may comprise a set of square waves applied at a frequency of 120 Hz, each square wave having an amplitude of 10 volts, and a pulse width of 1 millisecond. Another exemplary stimulus may include a set of square waves applied at a frequency of 2 Hz, each square wave having an amplitude of 20 volts and a pulse width of approximately 100 milliseconds.

Figure 5:
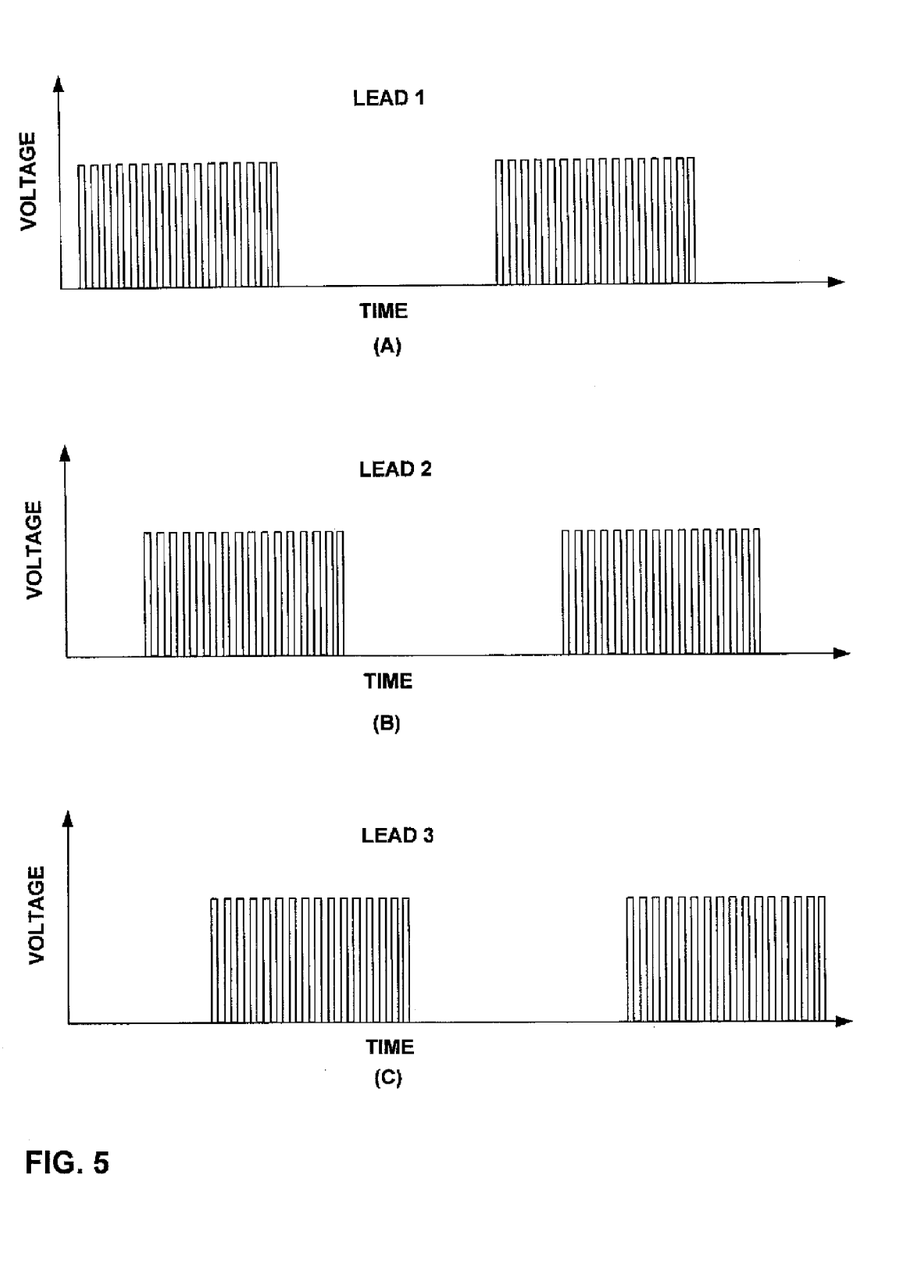
FIG. 5 is a timing diagram illustrating another exemplary stimulation algorithm for applying electrical stimuli to a colon of a patient via a plurality of leads.

FIG. 5 is a timing diagram illustrating another exemplary stimulation algorithm for applying electrical stimuli to colon 12 of a patient via a plurality of leads. As illustrated in the example of FIG. 5, colon stimulation system 10 applies electrical stimuli sequentially to colon 12 via leads 1, 2, and 3. Again, leads 1, 2, and 3 may correspond, for example, to leads 16A-16C illustrated in FIG. 1.

Like the stimulation algorithm in FIG. 4, colon stimulation system 10 applies, via each of the leads, a first set of electrical stimuli to colon 12. Colon stimulation system 10 removes the stimulation for a period of time, then applies a second set of electrical stimuli to colon 12. Unlike the stimulation algorithm depicted in FIG. 4, however, the stimulation algorithm shown in FIG. 5 applies the electrical stimuli to colon 12 sequentially instead of simultaneously. In other words, colon stimulation system 10 applies a first electrical stimulus to colon 12 via lead 1, a second electrical stimulus to colon 12 via lead 2 at a later time, and a third electrical stimulus to colon 12 via lead 3 at an even later time.

For example, colon stimulation system 10 may apply a first electrical stimulus to colon 12 via lead 1, wait 15 seconds, apply a second electrical stimulus to colon 12 via lead 2, wait 15 more seconds and apply a third electrical stimulus to colon 12 via lead 3. In other embodiments, colon stimulation system 10 may wait until the portion of colon 12 proximate the respective lead contracts to a certain point before delivering the subsequent stimulus. For example, colon stimulation system 10 may refrain from applying the second electrical stimulus to colon 12 until the portion of colon 12 proximate the first lead has contracted one-quarter of the way to the contracted state.

As described above, the length of time during which colon stimulation system 10 applies electrical stimuli to colon 12 may vary dramatically, e.g., between 10-90 seconds. Further, the length of the interval between applications of stimuli may also vary significantly. In the example of FIG. 5, the electrical stimuli applied to colon 12 are monophasic square waves. However, in other embodiments, other types of electrical stimuli may be applied to colon 12, including triangle waves, exponential decay waves, sine waves, and the like. Further, the electrical stimuli may be biphasic or triphasic.

Figure 6:
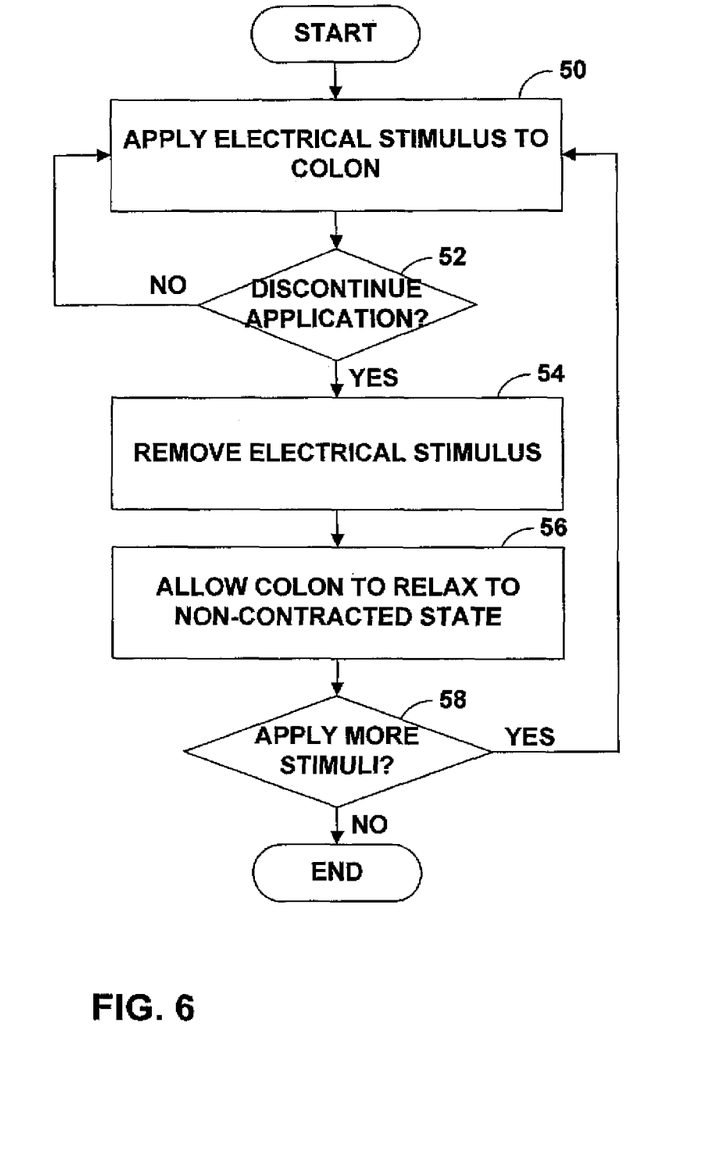
FIG. 6 is a flow diagram illustrating exemplary operation of a colon stimulation system stimulating a colon to induce peristaltic activity.

FIG. 6 is a flow diagram illustrating exemplary operation of a colon stimulation system, such as colon stimulation system 10 of FIG. 1, stimulating colon 12 to induce peristaltic activity. The peristaltic activity in colon 12 moves stool through colon 12 towards rectum 28 for exit out of a patient via anal canal 30.

Initially, colon stimulation system 10 applies an electrical stimulus to colon 12 of the patient via at least one of leads 16 and electrodes 17 (50). Colon stimulation system 10 applies an electrical stimulus generated by stimulus generator 14 to cecum 18 of colon 12, for example. However, colon stimulation system 10 may apply an electrical stimulus to other locations along colon 12 including ascending colon 20, transverse colon 22, descending colon 24 or sigmoid colon 26. The application of the electrical stimulus to colon 12 causes a portion of colon 12 proximate to electrodes 17 to contract to a contracted state.

Colon stimulation system 10 determines whether to discontinue application of the electrical stimulus to colon 12 (52), i.e., to remove the stimulus. Colon stimulation system 10 may determine to remove the stimulus based upon one or more criteria. Colon stimulation system 10 may include a timer and may be configured to apply the electrical stimulus to colon 12 for a defined time interval. Colon stimulation system 10 may discontinue application of the electrical stimulus upon expiration of the time interval. A typical time interval for application of the electrical stimulus to substantially fully contract a portion of colon 12 may be approximately sixty seconds.

In another variation, colon stimulation system 10 may include a sensor that generates a signal as a function of the contraction of colon 12. The sensor may, for example, sense one or more factors that change as a function of contraction of colon 12. A sensor may respond to a pressure in or proximate to colon 12, fore example, or a mechanical displacement of colon 12. Electrodes 17 may also be used as a sensor, as the impedance of electrodes 17 may change as a function of contraction of colon 12. Colon stimulation system 10 may determine to discontinue application of the electrical stimulus when a signal from the sensor indicates that the portion of colon 12 proximate electrodes 17 of lead 16 is substantially fully contracted. Colon stimulation system 10 may also determine to discontinue application of the electrical stimulus based upon a combination of time-based and sensor-based criteria, or based upon other criteria.

When colon stimulation system 10 removes the electrical stimulus (54), colon 12 relaxes (56). Contraction and relaxation of colon 12 may trigger natural peristaltic activity to relieve the patient from the discomfort due to chronic constipation. In some embodiments, colon stimulation system 10 allows colon 12 to relax to a substantially non-contracted state. However, in some cases, colon stimulation system 10 allows colon 12 relax, but not to relax to a fully non-contracted state.

A single colonic contraction, however, may not be enough to induce the peristaltic activity. Colon stimulation system 10 determines whether another electrical stimulus should be applied to colon 12 (58). Colon stimulation system 10 may, for example, administer a fixed number of stimuli, or apply additional stimuli when a signal from a sensor indicates peristaltic activity has not been induced. When another electrical stimulus is warranted, colon stimulation system 10 applies another electrical stimulus to colon 12 via electrodes 17 and leads 16 (50).

Figure 7:
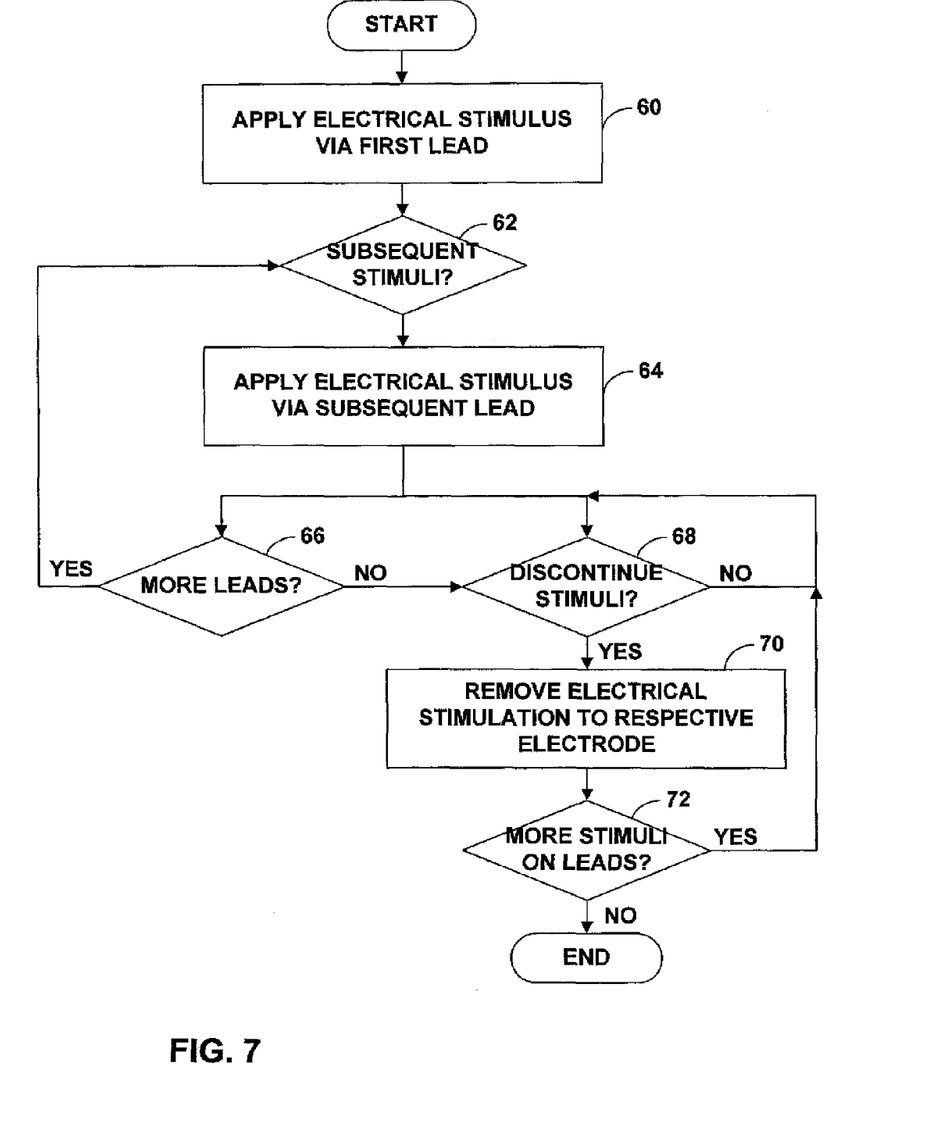
FIG. 7 is a flow diagram illustrating another exemplary operation of a colon stimulation system stimulating a colon to induce peristaltic activity.

FIG. 7 is a flow diagram illustrating another exemplary operation of a colon stimulation system, such as colon stimulation system 10 of FIG. 1, stimulating a colon to induce peristaltic activity. The contractions and relaxations of colon 12 in the stimulation algorithm illustrated in FIG. 7 "move" along colon 12 toward rectum 28.

Initially, colon stimulation system 10 applies a first electrical stimulus to colon 12 via a first lead and a first set of electrodes (60), e.g., lead 16C and electrodes 17E and 17F. Colon stimulation system 10 controls the timing of application of a subsequent electrical stimulus and applies at an appropriate time the subsequent electrical stimulus to colon 12 via a second lead and second set of electrodes (62, 64), e.g., lead 16B and electrodes 17C and 17D. For example, colon stimulation system 10 may apply the subsequent electrical stimulus to colon 12 following a defined time interval after commencement of application of the first electrical stimulus. Alternatively, colon stimulation system 10 may apply the subsequent electrical stimulus to colon 12 after the first electrical stimulus has caused the portion of colon 12 proximal to lead 16A to contract to a pre-defined degree. For instance, colon stimulation system 10 may apply a subsequent electrical stimulus to colon 12 after the portion of colon 12 proximate to electrodes 17E and 17F has contracted by approximately one quarter of a substantially full contraction.

Colon stimulation system 10 determines whether there are any leads 16 and electrodes 17 further along colon 12 and, concurrently, whether to discontinue any of the electrical stimuli (66, 68). When there are one or more leads 16 and electrodes 17 further along colon 12, colon stimulation system 10 determines when to apply an electrical stimulus and applies the electrical stimulus to colon 12 at the appropriate time via a lead and set of electrodes, e.g., lead 16A and electrodes 17A and 17B (62).

When there are no more leads and electrodes further along colon 12, colon stimulation system 10 determines whether any of the electrical stimuli applied via leads 16 and electrodes 17 should be discontinued (68). As described above, colon stimulation system 10 may determine that an electrical stimuli be discontinued based upon expiration of a timing interval measured by a timer, for example, or upon a signal from a sensor indicating a portion of colon 12 has reached a contracted state.

When colon stimulation system 10 determines that one or more electrical stimuli should be discontinued, colon stimulation system 10 removes the electrical stimulus from the respective lead to allow the colon to relax (70). As described above, colon stimulation system 10 may remove the electrical stimulus from the colon to allow the colon to relax to a fully non-contracted state. However, sometimes colon stimulation system 10 only allows the colon to relax to a partially non-contracted state, i.e., the colon is still partially contracted. Colon stimulation system 10 determines whether there are any more electrical stimuli being applied and whether the stimuli should be discontinued (72).

Colon stimulation system 10 may apply sets of sequential electrical stimuli in the same manner as described above. Colon stimulation system 10 may begin to apply the second set of electrical stimuli immediately after the last electrical stimuli of the first set are removed from the last of the subsequent leads. Alternatively, colon stimulation system 10 may wait a defined amount of time before applying the second set of electrical stimuli.

Various embodiments of the invention have been described. However, one skilled in the art will appreciate that the invention can be practiced with embodiments other than those disclosed.

The invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

The disclosed embodiments are presented for purposes of illustration and not limitation. These and other embodiments are within the scope of the following claims.

What is claimed is:

1. A method of inducing peristaltic activity in a colon comprising:
    applying an electrical stimulus to the colon with a pair of electrodes deployed diametrically opposite one another on the colon to cause a portion of the colon to contract to a contracted state, the portion of the colon being substantially fully contracted in the contracted state, each electrode of the pair of electrodes contacting slightly less than half of a circumference of the colon; and
    removing the electrical stimulus to cause the colon to relax.

2. The method of claim 1, wherein applying the electrical stimulus to the colon comprises applying the electrical stimulus to the colon for a duration of approximately 10 to 90 seconds.

3. The method of claim 2, wherein applying the electrical stimulus to the colon comprises applying the electrical stimulus to the colon for a duration of approximately 60 seconds.

4. The method of claim 1, wherein the electrical stimulus is a first electrical stimulus, the method further comprising applying a second electrical stimulus to the colon to cause the colon to contract to the contracted state after the colon has relaxed.

5. The method of claim 1, wherein the electrical stimulus is a first electrical stimulus, the method further comprising applying a second electrical stimulus to the colon substantially simultaneous with the first electrical stimulus.

6. The method of claim 1, wherein the electrical stimulus is a first electrical stimulus, the method further comprising applying a second electrical stimulus to the colon.

7. The method of claim 6, wherein the first and second electrical stimulus are applied to the colon via a common electrode.

8. The method of claim 6, wherein the first and second electrical stimulus are applied to the colon via a first and second electrode, and further comprising waiting a period of time between applying the first electrical stimulus and the second electrical stimulus.

9. The method of claim 1, wherein applying the electrical stimulus to the colon comprises applying the electrical stimulus to the colon with an electrode.

10. The method of claim 1, wherein applying an electrical stimulus to the colon comprises generating the electrical stimulus with an implanted stimulus generator.

11. The method of claim 10, wherein the implanted stimulus generator comprises a neurostimulator.

12. The method of claim 10, wherein the stimulus generator comprises an electrical pulse generator.

13. The method of claim 1, wherein applying the electrical stimulus to the colon comprises applying the electrical stimulus to a cecum of the colon.

14. The method of claim 1, wherein applying the electrical stimulus to the colon comprises applying the electrical stimulus to one of an ascending colon, a transverse colon, a descending colon, and a sigmoid colon.

15. The method of claim 1, wherein applying an electrical stimulus comprises applying a set of electrical stimuli.

16. The method of claim 1, wherein removing the electrical stimulus to cause the colon to relax comprises removing the stimulus to cause the colon to relax to a substantially fully non-contracted state.

17. A method of inducing peristaltic activity in a colon comprising:
    wrapping a pair of electrodes embedded within a patch body around a portion of a colon, the pair of electrodes are so sized and spaced along a contact side of the patch body such that the pair of electrodes are deployed diametrically opposite one another on the colon when the patch body is wrapped around the colon and each electrode of the pair of electrodes contacting slightly less than half of a circumference of the colon;
    applying an electrical stimulus to the colon with the pair of electrodes to cause a portion of the colon to contract to a contracted state, the portion of the colon being substantially fully contracted in the contracted state; and
    removing the electrical stimulus to cause the colon to relax.

18. The method of claim 17, wherein the pair of electrodes each have a length that extends along a common axis and a width that is less than the length and the width is perpendicular to the length.

19. The method of claim 17, wherein the pair of electrodes are wrapped around the colon to contact a substantial share of the circumference of the colon.

20. The method of claim 17, further comprising wrapping a second pair of electrodes around a portion of a colon, the second pair of electrodes are deployed diametrically opposite one another on the colon when the second pair of electrodes are wrapped around the colon;

applying an electrical stimulus to the colon with the second pair of electrodes to cause a portion of the colon to contract to a contracted state, the portion of the colon being substantially fully contracted in the contracted state after the colon is relaxed following the applying an electrical stimulus step to the first pair of electrodes; and removing the electrical stimulus to cause the colon to relax.

\* \* \* \* \*